US005756356A

United States Patent [19]

Yanagi et al.

[11] Patent Number: 5,756,356
[45] Date of Patent: May 26, 1998

[54] METHOD OF INDICATING TIME OR TEMPERATURE-TIME ACCUMULATED VALUE AS COLOR CHANGE, AND MATERIALS THEREFOR

[75] Inventors: Masato Yanagi; Makoto Dohi; Hideyuki Ishiguro; Keiichi Sato, all of Tokyo, Japan

[73] Assignee: Toyo Ink Manufacturing Co., Ltd., Tokyo, Japan

[21] Appl. No.: 622,140

[22] Filed: Mar. 27, 1996

[30] Foreign Application Priority Data

Mar. 31, 1995 [JP] Japan .................... 7-075279
Dec. 18, 1995 [JP] Japan .................... 7-328536

[51] Int. Cl.$^6$ .......................... G01N 31/00; G01N 21/00; G01K 3/00
[52] U.S. Cl. .................. 436/7; 436/1; 436/2; 436/164; 422/56; 422/57; 422/61; 422/119; 116/206; 374/106
[58] Field of Search .................. 436/1, 2, 164, 436/7; 422/56–58, 61, 119; 116/206; 374/106

[56] References Cited

U.S. PATENT DOCUMENTS

| | | | |
|---|---|---|---|
| 3,520,124 | 7/1970 | Myers | 368/92 |
| 3,888,631 | 6/1975 | Stürzinger | 116/207 |
| 3,966,414 | 6/1976 | Khattab et al. | 422/119 |
| 3,999,946 | 12/1976 | Patel et al. | 422/56 |
| 4,212,153 | 7/1980 | Kydonieus et al. | 368/62 |
| 4,276,190 | 6/1981 | Patel | 252/408 |
| 4,601,588 | 7/1986 | Takahara et al. | 374/106 |
| 4,729,671 | 3/1988 | Asano et al. | 374/106 X |
| 4,931,420 | 6/1990 | Asano et al. | 503/205 |
| 4,952,667 | 8/1990 | Shikatani et al. | 528/230 |
| 5,053,339 | 10/1991 | Patel | 436/2 |
| 5,057,434 | 10/1991 | Prusik et al. | 436/2 |
| 5,317,987 | 6/1994 | Müller et al. | 116/206 |
| 5,340,537 | 8/1994 | Barrett | 422/26 |

FOREIGN PATENT DOCUMENTS

| | | |
|---|---|---|
| 0 231 499 | 8/1987 | European Pat. Off. . |
| 53-80451 | 7/1978 | Japan . |
| 55-152059 | 11/1980 | Japan . |
| 4-313033 | 11/1992 | Japan . |
| 6-18676 | 1/1994 | Japan . |
| WO90/10868 | 9/1990 | WIPO . |

*Primary Examiner*—Arlen Soderquist
*Attorney, Agent, or Firm*—Wenderoth, Lind & Ponack

[57] ABSTRACT

A method of indicating a time or a temperature-time accumulated value as a color change (degree of color development), which comprises providing an oxidation-polymerizable dyestuff and the oxidizing agent in a non-contact state and bringing the oxidation-polymerizable dyestuff and the oxidizing agent into contact with each other to polymerize the oxidation-polymerizable dyestuff with the passage of time, and an indicator material therefor.

13 Claims, 2 Drawing Sheets

- TRANSPARENT SUBSTRATE
- OXIDATION-POLYMERIZABLE DYESTUFF
- OXIDIZING AGENT
- SUBSTRATE

- TRANSPARENT SUBSTRATE
- OXIDATION-POLYMERIZABLE DYESTUFF
- DIFFUSING LAYER
- OXIDIZING AGENT
- SUBSTRATE

- TRANSPARENT SUBSTRATE
- OXIDATION-POLYMERIZABLE DYESTUFF
- SPACER
- OXIDIZING AGENT
- SUBSTRATE

METHOD OF INDICATING TIME OR TEMPERATURE-TIME ACCUMULATED VALUE AS COLOR CHANGE, AND MATERIALS THEREFOR

BACKGROUND OF THE INVENTION

1. Field of the Invention

The present invention relates to a method of indicating a time or a temperature-time accumulated value as a change in color on the basis of the polymerization of an oxidation-polymerizable dyestuff, and materials used therefor.

2. Description of Related Art

In recent years, there are increasing demands for indicator materials for monitoring a temperature and a time when goods (articles) are stored at a constant temperature for a certain period of time. That is, generally, not only storage temperatures but also periods for use are indicated for chilled foods, frozen foods, perishable foods, medicines and chemical products such as coating compositions and adhesives. However, there is almost no method of measuring a temperature and a time as an accumulated value, and few indicator materials are commercially available.

As materials for indicating a temperature-time history as a change in color, U.S. Pat. Nos. 4,189,399 (issued Feb. 19, 1980), 4,208,186 (Jun. 17, 1980) and 4,276,190 (issued Jun. 30, 1980) disclose diacetylene-containing materials for indicating the passage of time, tens hours, at a temperature around 100° C. as a change in color from pink to metallic green. U.S. Pat. No. 4,212,153 (issued Jul. 15, 1980) discloses a dye which develops to a violet color on the basis of the diffusion of an acid or an alkali for indicating the passage of time, tens days, around room temperature. U.S. Pat. No. 3,768,976 discloses a redox dye which develops color on the basis of the diffusion of oxygen. U.S. Pat. No. 3,966,414 discloses a composition containing a dye having the sensitivity to a free radical and a peroxide, which indicates a temperature-time history by the fading of a green color. JP-A-62-190447 discloses a triaryl methane dye decolorized with a reducing agent, which is colored by the diffusion of oxygen. JP-A-5-61917 discloses oxygen-generating microorganism and a pH indicator. There are some other patent publications which use melting points, diffusion rates or active enzymes.

As described above, although a variety of indicator materials have been proposed, almost no indicator material is currently commercially available, presumably because either the handling thereof in a solution state is inconvenient, or the method of initiating the measurement of a time (temperature-time history) is complicated or unclear, or they are expensive. For example, in the invention using a dye having the sensitivity to a free radical and a peroxide (U.S. Pat. No. 3,966,414), an indicator material is a product in which a dye and a peroxide are supported on a glass fiber sheet. This indicator material is produced by dissolving the dye and the peroxide in a solvent and spreading the solution on the glass fiber sheet. In view of the measurement of time, a reaction is initiated at a point of time when the dye and the peroxide are dissolved, and the defect of this indicator material is that it is not actually suitable for the measurement of time at a temperature lower than room temperature. On the other hand, a color change utilized in most prior art techniques is a change in color from transparency to a certain color, or the fading of a certain hue toward transparency. There is therefore no indicator material which changes distinctly and drastically in color or hue.

The present inventors have sought to invent a method of, and an indicator material for indicating a time or a temperature-time accumulated value for displaying the passage of a predetermined period of time at a predetermined temperature by employing a simple and inexpensive method bringing two kinds of chemicals in a carrier into contact with each other. That is, the present inventors have sought to achieve the following: (1) No reaction is initiated until two kinds of chemicals in a carrier are brought into contact with each other. (2) The indicator material can be stored at room temperature. (3) The measurement is initiated at a point of time when the two chemicals are brought into contact. (4) The measurement can be initiated simply and distinctly.

Generally, not only storage temperatures but also periods for use are limited for chilled foods, frozen foods, perishable foods and chemical products such as coating compositions and adhesives. When these products are stored at a low temperature, most of them can be stored for a long period of time. As the temperature increases, the period for use dramatically decreases in many cases. However, most of the above products are generally controlled on the basis of the date of manufacture and the period of guarantee with a thermometer at a storage site. It is therefore unclear how long these products have been actually stored at a storage temperature. Further, there is no inexpensive system for monitoring environments in which individual products are placed when the products are transported from one site to another at a predetermined temperature for a predetermined period of time in a distribution process.

It is therefore desired to develop a method of, and an indicator material for, distinctly and inexpensively indicating, through a total sum of quantity of heat, how long individual products are stored at a predetermined temperature or a how long and at what temperature individual products are stored.

SUMMARY OF THE INVENTION

It is an object of the present invention to provide a method of indicating a time or a temperature-time accumulated value as a color change (degree of color development) and an indicator material therefor.

It is another object of the present invention to provide a method of indicating a time or a temperature-time accumulated value as a color change (degree of color development) and an indicator material therefor, which enable the control of time-temperature when it is required to control the time-temperature for various products of which the production step, distribution and use period are limited.

According to the present invention, there is provided a method of indicating a time or a temperature-time accumulated value as a color change, which comprises providing an agent A and an agent B in a non-contact state and bringing the agent A and the agent B into contact with each other to polymerize an oxidation-polymerizable dyestuff, wherein the agent A is the oxidation-polymerizable dyestuff or an oxidizing agent and the agent B is an oxidizing agent when the agent A is the oxidation-polymerizable dyestuff or the oxidation-polymerizable dyestuff when the agent A is the oxidizing agent.

Further, according to the present invention, there is provided an indicator material formed of a carrier, an agent A and an agent B, the agent A and the agent B being in a non-contact state and the agent A and/or the agent B being held in the carrier, for indicating a time or a temperature-time accumulated value as a color change by bringing the agent A and the agent B into contact with each other to polymerize an oxidation-polymerizable dyestuff, wherein the agent A is the oxidation-polymerizable dyestuff or an oxidizing agent and the agent B is an oxidizing agent when the agent A is the oxidation-polymerizable dyestuff or the oxidation-polymerizable dyestuff when the agent A is the oxidizing agent.

DETAILED DESCRIPTION OF THE INVENTION

The present inventors have found that a color change (color development) corresponding to a polymerization degree is generated when an oxidation-polymerizable dyestuff and an oxidizing agent are used. Like general reactions, the polymerization rate is defined by a temperature and a time according to Arrhenius' equation. It has been therefore found that a temperature-time accumulated value which may be called a total sum of a change of time and a quantity of heat at a predetermined temperature can be indicated as a change in color. On the basis of this finding, the present invention has been arrived at.

Figure 2:
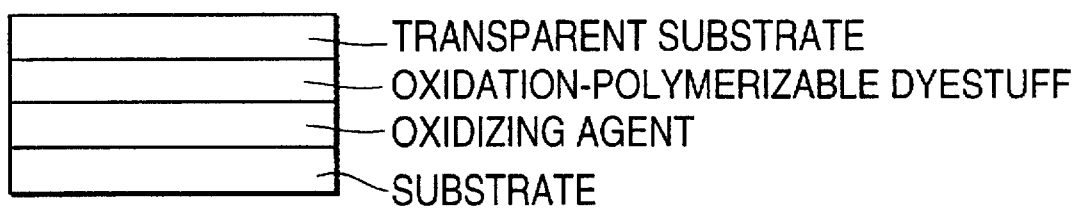
FIG. 2 shows the layers forming the indicator material during contact state.
Figure 3:
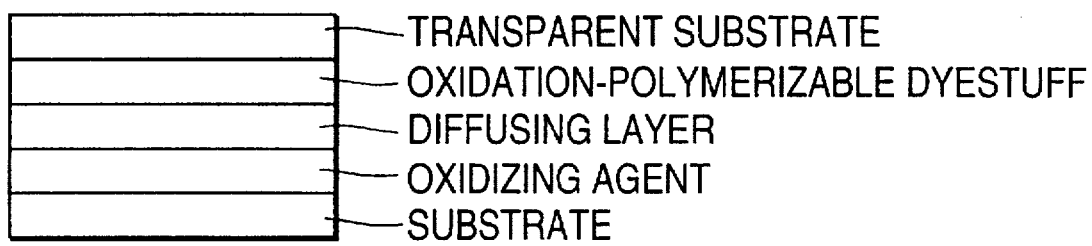
FIG. 3 shows the layers forming the indicator material during diffusion state.

The oxidation-polymerizable dyestuff used in the present invention is a compound which initiates a reaction of polymerization by being brought into contact with an oxidizing agent (see FIG. 2). It then undergoes a polymerization and develops a predetermined hue at a predetermined polymerization degree. Before the polymerization, the oxidation-polymerizable dyestuff may be colorless or colored.

Like general chemical reactions, the rate of the above polymerization is defined by a difference in temperature. Further, the oxidation-polymerizable dyestuff used in the present invention is a dyestuff which changes in hue or color density depending upon the polymerization degree, and the hue is defined by a temperature and a time. That is, the polymerization rate follows Arrhenius' equation, and the polymerization degree of the dyestuff is therefore defined as a function of absolute temperature and time. As a result, a time or a temperature-time accumulated value can be indicated as a color change.

The quantity of heat at a constant temperature or at varying temperatures can be expressed as an integrated value obtained by a product in temperature at a point of time and time. The integrated value of temperature and time is defined to be the temperature-time accumulated value.

For example, the consumption period or use period of meat or fish as a chilled food differs depending upon a storage temperature, e.g., 12 hours at 30° C., 24 hours at 20° C. or 72 hours at 10° C. It can also be considered that the storage temperature during actual distribution constantly changes although that degrees of the change differ. In this case, it is important to measure "at what temperatures and how long the food is left or stored". The temperature-time accumulated value can work as a scale for the above measurement.

In the present invention, the hue changes depending upon the degree of polymerization of a polymer obtained by the polymerization of the oxidation-polymerizable dyestuff. For example, when the oxidation-polymerizable dyestuff is 2-methoxy-phenothiazine, it is considered that the color development (change in hue) takes place in the following mechanism.

Figure 1:
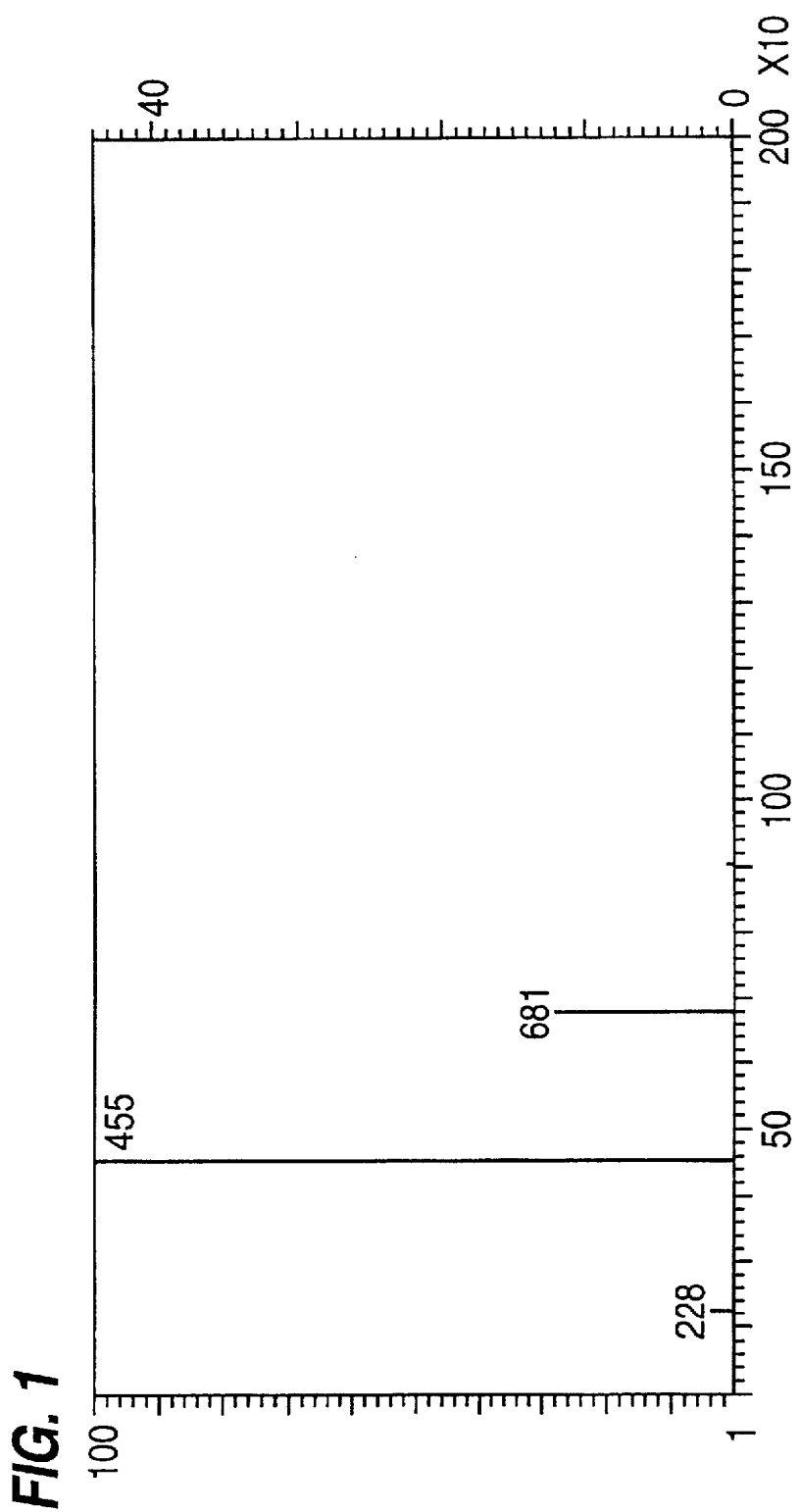
FIG. 1 shows a mass spectrum at an initial stage of a reaction between 2-methoxy-phenothiazine and copper chloride.

Hydrogen atom bonding to nitrogen atom in the molecule of the oxidation-polymerizable dyestuff is withdrawn by the oxidizing agent. Further, oxygen atom on any one of the 1, 3, 4, 6, 7, 8 and 9 positions on the 2-methoxy-phenothiazine molecule is withdrawn, whereby the polymerization is initiated. It is assumed that the above molecule and an adjacent molecule undergo polymerization with nitrogen atom on the 10-position and carbon atom from which hydrogen atom has been withdrawn being binding sites. FIG. 1 shows a mass spectrum at an initial stage of the polymerization of 2-methoxy-phenothiazine which is polymerized in the presence of copper chloride (II) as an oxidizing agent in Example 1. The reaction mechanism is not clear in detail, while FIG. 1 clearly shows that 2-methoxy-phenothiazine is polymerized by a reaction between the oxidizing agent and the 2-methoxy-phenothiazine.

It is considered that the hue changes since the conjugated system changes as the polymerization of 2-methoxy-phenothiazine proceeds. That is, it is assumed that the hue shifts toward a long wavelength side, from green to reddish brown, with an increase in the degree of polymerization.

In the relationship of the hue and polymerization degree of the 2-methoxy-phenothiazine, it has been found on the basis of visually evaluated hue and molecular weights from a mass spectrometer that the 2-methoxy-phenothiazine develops green at a polymerization degree of 2, blue at a polymerization degree of 3 and reddish brown at a polymerization degree of 4 to 10. It is also analogically reasoned that the 2-methoxy-phenothiazine develops deep blue or violet depending upon the distribution of polymerization degree.

In other phenothiazine derivatives and phenoxazine derivatives, the electron state of conjugated system greatly differs depending upon substituents bonding to the phenothiazine skeleton, and it has been observed that these derivatives show a hue change which differs depending upon substituents.

In any case, the hue to be developed is determined depending upon the polymerization degrees of phenothiazine derivatives and phenoxazine derivatives and distributions of the polymerization degrees, and the hue changes as the polymerization proceeds. The molecular structure of the 2-methoxy-phenothiazine and positions of constituent atoms thereof are represented by the following formula.

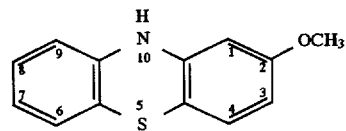

The oxidation-polymerizable dyestuff used in the present invention is not specially limited so long as it undergoes oxidation-polymerization and develops a predetermined hue at a predetermined polymerization degree. The oxidation-polymerizable dyestuff refers to a dyestuff which undergoes oxidation polymerization in the presence of an oxidizing agent typified by a metal salt and develops a predetermined hue at a predetermined polymerization degree. The oxidation-polymerizable dyestuff therefore includes those which are colorless before the polymerization but develops a hue after it is polymerized. Specific examples of the oxidation-polymerizable dyestuff include benzene derivatives such as aniline, phenol, thiophenol and derivatives of these; five-membered heterocyclic compounds such as pyrrole, thiophene, furan, selenophene and derivatives of these; fused 6, 5, 6-membered aromatic heterocyclic compounds such as carbazole, dibenzothiophene and derivatives of these and compounds of the following formula (1),

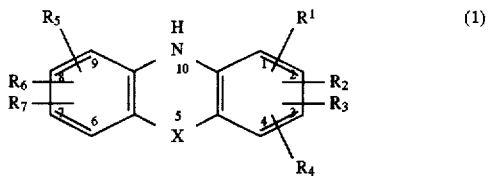

wherein each of $R_1$ to $R_7$ is independently hydrogen, halogen, an alkyl group having 1 to 8 carbon atoms, aryl, substituted aryl, heterocyclic aryl, hydroxyl, amino, cyano, aldehyde, carbonyl or nitro, provided that a combination of adjacent substituents may form an aromatic ring, and X is sulfur, oxygen, selenium or tellurium.

The positions on which of $R_1$ to $R_4$ are substituted are 1-, 2-, 3- and 4-positions in the formula (1). In no case, however, two or more substituents of $R_1$ to $R_4$ are substituted on one position, and one substituent is substituted on one position. Similarly, the positions on which $R_5$ to $R_7$ are substituted are three positions of the 6-, 7-, 8- and 9-positions. In no case, however, two or more substituents of $R_5$ to $R_7$ are substituted on one position, and one substituent is substituted on one position. In addition to the above substituents as $R_1$ to $R_7$, each of $R_1$ to $R_7$ may be other substituent so long as the substituent does not impede the polymerization.

Specific examples of the compound of the formula (1) include phenothiazine, 3,7-dibromoophenothiazine, 2-chlorophenothiazine, 4-methylphenothiazine, 3,7-dimethylphenothiazine, 4,6-dimethylphenothiazine, 2-acetylphenothiazine, 3-vinylphenothiazine, 3,7-diaminophenothiazine, 3,7-bis-(dimethylamino)-phenothiazine, 3,7-bis-(diethylamino)-phenothiazine, 2-hydroxy-phenothiazine, 3-formyl-phenothiazine, 3-carboxyl-phenothiazine, 3,7-dimethoxy-phenothiazine, 1-nitro-phentothiazine, 1,3-dinitro-phenothiazine, 4-chloro-1-nitro-phenothiazine, and benzophenothiazines such as monobenzo-phenothiazine disclosed in JP-A-3-144650 in which a combination of adjacent two substituents of $R_1$ to $R_4$ forms an aromatic ring and dibenzo-phenothiazine disclosed in JP-A-3-144650 in which a combination of adjacent two substituents of $R_1$ to $R_4$ forms an aromatic ring and a combination of adjacent two substituents of $R_5$ to $R_7$ forms an aromatic ring.

Further, the oxidation-polymerizable dyestuff used in the present invention includes phenoxazine derivatives including phenoxazine and 3,7-dibromophenoxazine.

The above phenothiazines and phenoxazines can be synthesized by the method described in "Dai-Yuuki Kagaku (Great Organic Chemistry)", Vol. 17, Heterocyclic Compound IV-A, pages 33 and 17, M. Kotake (Asakura Publishing Co.).

The above oxidation-polymerizable dyestuffs may be used alone or in combination. The hue can be adjusted (changed) on the basis of the mixing ratio of the oxidation-polymerizable dyestuffs.

The amount of the oxidation-polymerizable dyestuff per 100% by weight of the carrier is 1.0 to 20% by weight, preferably 2.0 to 15.0% by weight. When the amount of the oxidation-polymerizable dyestuff is smaller than the above lower limit, the color development is too low to evaluate it visually. When the amount of the oxidation-polymerizable dyestuff is larger than the above upper limit, there is almost no further change in the degree of color development, while the indicator material may develop a color due to the oxidation with oxygen in air when stored and therefore, may be no longer used.

The oxidizing agent used for polymerizing the oxidation-polymerizable dyestuff in the present invention includes metal salts, oxyacid salts, halogens, dimethyl sulfoxides, quinones, naphthoquinones, carbonyl compounds, oxides, organic peroxides, organic peracids, peroxysulfates and nitro compounds. Specific examples of the metal salts include aluminum chloride, nickel chloride, cobalt chloride, copper chloride, iron chloride and vanadium chloride. Specific examples of the oxyacids salts include nitrate, chlorate, hypochlorate, iodate, bromate, chromate, permanganate, vanadate and bismuthate. Specific examples of the halogens include fluorine, chlorine, bromine and iodine. Specific examples of the quinones include benzoquinone, tetrachloro-1,4-benzoquinone, tetrachloro-1,2-benzoquinone) and 2,3-dichloro-5,6-dicyano-1,4-benzoquinone. Specific examples of the naphthoquinones include 1,2-naphthoquinone, 1,4-naphthoquinone, 2,6-naphthoquinone and 1,2-naphthoquinone-4-sulfonic acid. Specific examples of the carbonyl compounds include acetone and cyclohexanone, and these carbonyl compounds are used in combination with aluminum alkoxide such as aluminum butoxide. Specific examples of the oxides include manganese dioxide, lead dioxide, copper oxide and silver oxide. Specific examples of the organic peroxides include dialkyl peroxides such as di-tert-butyl peroxide, tert-butylcumyl peroxide and dicumyl peroxide, diacyl peroxides such as acetyl peroxide, lauroyl peroxide and benzoyl peroxide, ketone peroxides such as methyl ethyl ketone peroxide, cyclohexanone peroxide, 3,3,5-trimethylcyclohexanone peroxide and methylcyclohexanone peroxide, peroxy ketals such as 1,1-bis(tert-butylperoxy) cyclohexane, hydroperoxides such as tert-butyl hydroperoxide, cumene hydroperoxide, 1,1,3,3-tetramethylbutyl hydroperoxide, p-menthane hydroperoxide, diisopropylbenzene hydroperoxide and 2,5-dimethylhexane-2,5-dihyroperoxide, and peroxy esters such as tert-butyl peroxyacetate, tert-butyl peroxy-2-ethylhexanoate and tert-butylperoxybenzoate. Of the above peroxides, benzoyl peroxide is particularly preferred since it is well-balanced between oxidation reactivity and storage stability. Specific examples of the organic peracids include perbenzoic acid, m-chloroperbenzoic acid, monoperoxyphthalic acid, performic acid, peracetic acid and trifluoroperacetic acid. Specific examples of the peroxosulfates include peroxodisulfuric acid and potassium peroxodisulfate. Specific examples of the nitro compounds include nitrobenzene, nitrogylcerine and nitrocellulose. Further, the oxidizing agent used in the present invention includes oxygen, ozone, chlorine, bromine, iodine, sulfur, aqua regia, nitric acid, concentrated sulfuric acid, hot concentrated perchloric acid, dimethyl sulfoxide and siliver carbonate. Further, the oxidizing agent used in the present invention can be also selected from biochemical oxidizing agents such as dehydrogenase.

The carrier used in the present invention refers to a substrate which is inert to the oxidation-polymerization dyestuff and the oxidizing agent and can diffuse them under predetermined conditions. For example, when the carrier is a resin, the resin can be selected from those which can permit the diffusion of the oxidation-polymerizable dyestuff and the oxidizing agent in a predetermined temperature range, which can retain a form, e.g., the form of a layer and which has transparency adequate for the recognition of a change in color. The carrier can be also selected from liquid media.

Specific examples of the carrier include resins used as a binder for general inks and coating compositions, such as an acrylic resin, a polyester resin, a polyether resin, a polyurethane resin, a silicone resin, an epoxy resin and a vinyl resin and adhesive rubber-based resins used as a general adhesive mass. These carriers may be used alone or in combination, and the carrier may be diluted with a generally used solvent such as any one of ketones, ethers, alcohols, cellosolve solvents, petroleum solvents and aqueous solvents.

In particular, the adhesive rubber-based resin is preferred since it exhibits the function of bonding the carrier and a transparent substrate to each other.

The above rubber-based resin specifically refers to a resin which has a Tg equivalent to, or lower than, room temperature, preferably a Tg of $-10°$ C. or lower, and which is in a rubbery state at a temperature when the indicator material is used. Examples of the rubber-based resin include an adhesive acrylic resin, natural and synthetic cis-1,4-polyisoprene rubbers, butyl rubber, halogenated butyl rubber, partially vulcanized butyl rubber, a styrene-butadiene-styrene block copolymer (SBS), a styrene-isoprene-styrene block copolymer (SINTERED SUBSTRATE), a styrene-ethylene-butylene-styrene block copolymer (SEBS), silicone rubber, chloroprene rubber, nitrile rubber and butadiene rubber. Of these, an adhesive acrylic resin is one of the most suitable carriers for the indicator material since the Tg of the adhesive acrylic resin can be adjusted (changed) as required by properly adjusting its composition and molecular weight so as to control the diffusion rate of the agent A or B. The adhesive acrylic resin refers to resins which have functional groups such as hydroxyl, tertiary amino, carboxyl, amide and nitrile and which are generally used as acrylic resins for adhesive mass. The adhesive acrylic resin is a copolymer produced by the copolymerization of at least one of monomers having hydroxyl, tertiary amino, carboxyl, amide and nitrile groups and at least one monomer of alkyl (meth)acrylate, vinyl acetate, vinyl propionate, vinyl ether and styrene.

The above copolymerization is a general radical polymerization and the reaction method therefor is not specially limited. The polymerization can be carried out by any one of known methods such as solution polymerization, bulk polymerization and emulsion polymerization, while the solution polymerization method is preferred since it is easy to control the reaction and since a subsequent procedure can be directly continued. Any solvent may be used so long as the above resin can be dissolved. The solvent includes methyl ethyl ketone, methyl isobutyl ketone, toluene, cellosolve, ethyl acetate and butyl acetate. These solvent may be used alone or in combination. Further, the copolymerization is carried out in the presence of a polymerization initiator selected from known polymerization initiators. The polymerization initiator is not specially limited, and can be selected from organic initiators such as benzoyl peroxide, acetyl peroxide, methyl ethyl ketone peroxide and lauroyl peroxide, and azo initiators such as azobisisobutyronitrile.

The adhesive rubber-based resin may be partially crosslinked with a crosslinking agent such as isocyanate or an epoxy compound for improving the carrier in adhesion and cohesive power or for adjusting the diffusion rate of the agent A or B.

Further, a polyurethane resin is one of preferred carriers in view of productivity of the indicator material, since it has excellent printability for gravure printing, etc. The polyurethane resin is available in the trade names of "Lamistar R Medium", "New LP Super" and "LP Queen" (supplied by Toyo Ink Manufacturing Co., Ltd.).

Figure 4:
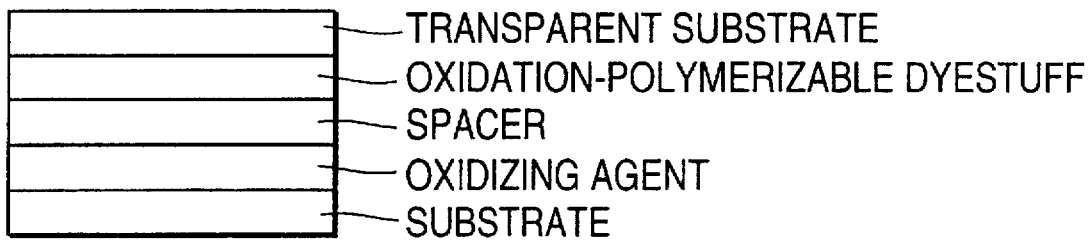
FIG. 4 shows the layers forming the indicator material during non-contact state.

In the indicator material of the present invention, the agent A and the agent B are held in carriers in a non-contact state. For example, the indicator material is formed of a first layer containing the agent A held in a carrier, a second layer containing the agent B held in a carrier in a non-contact state with the agent A and a third layer (spacing layer) which is present between the first and second layers and through which the agent A or B is diffused (see FIG. 4). Like the carriers for the above first layer and the above second layer, the above third layer is that which can permit the diffusion of at least one of the oxidation-polymerizable dyestuff and the oxidizing agent as agents A and B in a predetermined temperature range, which can retain a form, e.g., the form of a layer, and which has transparency which makes it possible to recognize a change in color (see Fig.). Further, the third layer is required to have the following function. No diffusion of the agents A and B, i.e., the oxidation-polymerizable dyestuff and the oxidizing agent takes place at a storage temperature before use, and the time measurement is initiated at a point of time when a predetermined temperature is reached.

Specifically, examples of the material for the third layer include resins used as a binder for general inks and coating compositions, such as an acrylic resin, a polyester resin, a polyether resin, a polyurethane resin, a silicone resin, an epoxy resin and a vinyl resin and adhesive rubber-based resins used as a general adhesive mass. These materials may be used alone or in combination, and the material may be diluted with a generally used solvent such as any one of ketones, ethers, alcohols, cellosolve solvents, petroleum solvents and aqueous solvents.

In particular, the structure and the molecular weight of the acrylic resin can be adjusted as required so as to adjust its Tg, and the diffusion rate of the agent A or B in the acrylic resin can be controlled. The acrylic resin is therefore suitable for the third layer. The acrylic resin can be synthesized in the same manner as in the synthesis of the adhesive acrylic resin used as the typical carrier for the above first and second layer except for the following. The adhesive acrylic resin has a Tg equivalent to, or lower than, room temperature, preferably $-10°$ C. or lower, while the acrylic resin for the third layer differs in monomer composition in that the acrylic resin has a Tg suited to a temperature range in which the indicator material is used.

Further, in view of the control of the diffusion rate, the third layer may be formed of a blend of a generally used resin including the acrylic resin with a substance having high sensitivity to temperature such as a thermotropic liquid crystal, a plasticizer or a wax.

When the indicator material of the present invention is formed, for example, by laminating the first layer containing the agent A held in the carrier, the second layer containing the agent B held in the carrier and a spacing material which keeps the two layers in a non-contact state and can bring these two layers into contact under an external pressure, the spacer material include a woven fabric, a nonwoven fabric, a powder and microcapsules. In the present invention, the agent A and the agent B are held in a non-contact state to each other before use, and the agents A and B, the carrier containing the agent A and the carrier containing the agent B, or the carrier containing the agent A or B penetrate(s) the spacer material when an external pressure is exerted. As a result, the agent A and the agent B are brought into contact. Otherwise, the spacer material is broken when an external pressure is exerted, and as a result, the agent A and the agent B are brought into contact. In the present invention, any other method may be employed so long as the agent A and the agent B can be brought into contact with each other.

A general cloth of loose texture such as gauze is used as a woven fabric. Examples of the woven fabric include a staple fiber woven fabric 40 filaments/inch×28 filaments/inch, a staple fiber 40/1 (supplied by Aoyama Sangyo K.K.), a staple fiber woven fabric 45 filaments/inch×35 filaments/inch, a staple fiber 30/1 (Aoyama Sangyo K.K.), a PET woven fabric 45 filaments/inch×35 filaments/inch, PET 80 d special yarns×100 d processed yarn (Aoyama Sangyo K.K.), a PET woven fabric 45 filaments/inch×30 filaments/inch and PET 80 d special yarns×100 d processed yarns (Aoyama Sangyo K.K.). Examples of the nonwoven include Rayon 50% nonwoven fabric (basis weight 10 g/m$^2$, supplied by Daio Paper Corporation), Rayon 50% nonwoven fabric (basis weight 17 g/m$^2$, Daio Paper Corporation), Rayon 50% nonwoven fabric (basis weight 30 g/m$^2$, Daio Paper Corporation), Vinylon 70% nonwoven fabric (100 µm, Daio Paper Corporation), Vinylon 100% nonwoven fabric (100 µm, Daio Paper Corporation) and a polyester nonwoven fabric. Examples of the powder include fine powders of metals or metal oxides such as aluminum, copper, silver, gold, silicon dioxide typified by Aerosil, titanium dioxide, Shirasu (volcanic ash occurring in the Southern part of Japan) and diatomaceous earth, microspheres of polymers such as a nylon powder, a polyethylene powder, polystyrene beads and acryl beads, and edible powders having a particle diameter of tens to hundreds µm such as flour, dogtooth violet starch and potato starch.

Examples of the microcapsules include microcapsules obtained by an interfacial polymerization method disclosed in Japanese Patent Publications Nos. 38-19574, 42-446, 42-2882 and 42-2883, JP-B-56-11537 and JP-B-60-60173, an in-situ polymerization method disclosed in Japanese Patent Publication No. 36-9168, U.S. Pat. No. 3,427,250 and BP 1,236,498, an in-liquid curing coating method disclosed in U.S. Pat. Nos. 3,787,327, 3,551,346 and 3,574,133, a coacervation method (phase separation method) disclosed in U.S. Pat. Nos. 2,800,457, 3,531,418 and, 3,577,515 and BP 1,117,178, an interfacial precipitation method disclosed in U.S. Pat. Nos. 3,523,906 and 3,660,304, and a spray-dry method disclosed in U.S. Pat. No. 3,830,750, and hollow glass spheres, Shirasu balloons, alumina bubbles and phenol microballoons described in "New Microcapsules—Process, Properties and Applications", T. Kondo, et al (Sankyo Publishing Co.).

When the agent A and the agent B are held in a carrier and when one of the agents A and B is microencapsulated, the method of microencapsulating the agent A or B is not specially limited, and the agent A or B may be microencapsulated by any one of the above methods for microencapsulating the spacer material.

Preferably, the agent A or B is microencapsulated by an interfacial polymerization method in which microcapsule walls are formed of polyurea. Since, in this method, the thickness of the microcapsule walls can be adjusted as required, uniform microcapsule walls can be formed and the strength of the microcapsule walls can be increased.

The carrier used in the present invention may contain a dye, an inorganic filler, a metal powder such as a silver powder, a copper powder or a nickel powder, carbon black, graphite, a xylene resin-based or rosin-based tackifier, a silane coupling agent, a defoaming agent and a leveling agent.

When an inorganic additive such as Aerosil, titanium dioxide or barium sulfate is added, the carrier is improved in cohesive strength, tacking on the carrier surface is decreased, there is exhibited an effect that the inorganic additive controls the diffusion rate of the agent A or B, i.e., the oxidation-polymerizable dyestuff or the oxidizing agent, by adsorbing the agent A or B, and the indicator material has an effect that the range of measurement of the temperature-time accumulated value is broadened. Further, Aerosil alters the hue when combined with some oxidizing agent, and broadens the range of measurement of the temperature-time accumulated value.

The method of preparing the indicator material is not specially limited so long as it is formed as a layer holding the agent A or the agent B and so long as the agent A and the agent B are held in the carrier in a non-contact state. For example, the indicator material is obtained by a coating method using a lip coater or a kiss coater used for preparing an adhesive mass, by a printing method using a source marking ink such as a gravure ink, an offset ink, a screen ink, a lithographic ink or a flexographic ink as a carrier, or by a printing method using an on-demand ink such as a stamp ink, a carbon-free paper ink, an inkjet ink, a wire dot ink, a typewriter ink or a thermal ink. These methods may be used alone or in combination. For example, a layer containing the agent B may be directly formed on the surface of a taped-shaped layer containing the agent A by a printing method just before the initiation of the measurement of a temperature-time accumulated value. A layer containing the agent A may be formed on a transparent substrate by a printing method and the resultant laminate may be attached to the surface of a taped-shaped layer containing the agent A just before the initiation of the measurement of a temperature-time accumulated value.

Further, the layer holding the agent A or B may be formed by a method such as solid application of the agent/solid application of the carrier, solid application of the agent/pattern of the carrier or pattern of the agent/pattern of the carrier. A portion which shows a color change for showing a temperature-time accumulated value may be formed as an image. Further, a transparent film having a hue of a complimentary color to a color obtained by the color change of the indicator material may be used as a cover, for displaying "expiration of consumption period" or "ready to eat" in a predetermined temperature-time accumulated value.

The indicator material of the present invention may be prepared in the following form. That is, the agent A and the agent B, i.e., the oxidation-polymerizable dyestuff and the oxidizing agent, are independently placed in different containers such as glass bottles, and diluted with a generally used solvent such as a ketone solvent, an ether solvent, an alcohol solvent, a cellosolve solvent, a petroleum solvent or an aqueous solvent. Further, for example, a felt is impregnated with a solution containing the agent A and formed into a felt-tipped marker, and an image is formed on a layer containing the agent B with the felt-tipped marker so that the agent A and the agent B are brought into contact. Further, a felt is impregnated with a solution containing the agent A and formed into a felt-tipped marker, a felt is impregnated with a solution containing the agent B and formed into a felt-tipped marker, and overlapped images are formed with these markers so that the agent A and the agent B are brought into contact.

In the present invention, a layer containing the agent A or B may be formed on a transparent film. The transparent substrate is selected from a film of an olefin such as polyethylene or polypropylene, a film of a polyester typified by polyethylene terephthalate, and a film of a plastic such as cellophane, polyvinylidene chloride, a polyvinylidene chloride copolymer, polyvinylidene fluoride, polyvinyl chloride or polyacrylic acid, polymethacrylic acid.

Further, the transparent substrate may be selected from other materials so long as a hue change can be recognized.

In the present invention, a layer containing the agent A and a layer containing the agent B may be formed by any one of a silk screen printing method, a gravure printing method and an offset printing method. The printing method and the binder used for the printing are not specially limited so long as the above layers can be formed.

The field where the indicator material of the present invention is used is not specially limited. The indicator material of the present invention can be used for controlling the consumption periods and the temperature-time for various products having limited consumption periods and various products which require the control of time-temperature in a production step, a distribution process, storage and use by attaching it to the products. It is used for controlling the consumption periods and the temperature-time for chilled or frozen foods such as chilled or frozen beef, ham, chicken and fishes, frozen vegetables, frozen processed foods, dairy products, beverages, perishables, cakes, liquors, fluits, chemical products, medicines, implantation-related organs, and the like.

EXAMPLES

The present invention will be explained in detail with reference to Examples hereinafter, in which "part" stands for "part by weight" and "%" stands for "% by weight".

Preparation Example 1 (Resin 1)

A mixture containing 47.05 parts of butyl acrylate, 2.95 parts of acrylic acid 0.1 part of azobisisobutyronitrile and 75 parts of ethyl acetate was placed in a flask and heated to 80° C. in a nitrogen atmosphere, and the same mixture as the above mixture was dropwise added, and then the resultant mixture was refluxed under heat at 80° C. for 12 hours and then cooled to give a solution of resin 1 (solid content 40%).

Preparation Example 2 (Resin 2)

A mixture containing 50 parts of butyl acrylate, 0.1 part of azobisisobutyronitrile and 75 parts of ethyl acetate was placed in a flask and heated to 80° C. in a nitrogen atmosphere, and the same mixture as above was dropwise added, and then the resultant mixture was refluxed under heat at 80° C. for 12 hours and then cooled to give a solution of resin 2 (solid content 40%).

Example 1

100 Parts of the solution of resin 1 and 12 parts of an ethyl acetate solution containing 10% of 2-methoxyphenothiazine were mixed with stirring, and the mixture was applied to a silicone-coated PET film with a doctor blade and dried under heat at 90° C. for 2 minutes to form a 25 μm thick layer containing agent A. Separately, 100 parts of the solution of resin 1 and 2 parts of copper chloride (II) were mixed with stirring, and the mixture was applied to a silicone-coated PET film and dried under heat at 90° C. for 2 minutes to form a 25 μm thick layer containing agent B. The layer containing agent A and the layer containing agent B were attached, to obtain an indicator material 1. The point of time when the above layers were attached was a time at which the measurement was initiated. The indicator material was observed for a color change with time under the following conditions. Table 2 shows the results.

(1) Color change with time

The point of time when the layer containing agent A and the layer containing agent B were attached was a time at which the measurement was initiated. The same indicator materials at that obtained in the above manner were separately stored in constant-temperature chambers at 0° C., 20° C. and 100° C., and observed for changes in color with time.

Examples 2–15 and Comparative Examples 1–2

In the same manner as in Example 1, an ethyl acetate solution containing 10% of a oxidation-polymerizable dyestuff and a solution of a resin shown in Table 1 were mixed in amounts shown in Table 1 with stirring, and the mixture was applied to a silicone-coated PET film with a doctor blade and dried under heat at 90° C. for 2 minutes to form a 25 μm thick layer containing agent A. Further, in the same manner as in Example 1, an oxidizing agent and a solution of a resin shown in Table 1 were mixed in amounts shown in Table 1 with stirring, and the mixture was applied to a silicone-coated PET film with a doctor blade and dried under heat at 90° C. for 2 minutes to form a 25 μm thick layer containing agent B. The layer containing agent A and the layer containing agent B were attached to use these layers as an indicator material. The point of time when the above layers were attached was a time at which the measurement was initiated. The indicator material was observed for a color change with time in the same manner as in Example 1. Table 2 shows the results. The amounts shown in Table 1 are amounts as solids. The amounts as solids do not simply refer to insoluble contents, but refer to amounts of components after the mixtures were dried under heat, that is, amounts of solids remaining after the mixtures were dried under heat.

Example 16

100 Parts of the solution of resin 1 and 12 parts of an ethyl acetate solution containing 10% of 2-methoxyphenothiazine were mixed with stirring, and the mixture was applied to a silicone-coated treated PET film with a doctor blade and dried under heat at 90° C. for 2 minutes to form a 25 μm thick layer containing agent A. Separately, 100 parts of a urethane resin (solid content 40%, Lamistar R Medium, supplied by Toyo Ink Manufacturing Co., Ltd.,) for gravure ink and 2 parts of copper chloride (II) were mixed with stirring, and the mixture was applied to a transparent PET film by carrying out gravure printing 10 times and dried under heat at 90° C. for 2 minutes to form a 25 μm thick layer containing agent B. The layer containing agent A and the layer containing agent B were attached to use these layers as an indicator material. The point of time when the above layers were attached was a time at which the measurement was initiated. The indicator material was observed for a color change with time in the same manner as in Example 1. Table 2 shows the results.

TABLE 1

| | Layer containing agent A | | | | Layer containing agent B | | | |
| --- | --- | --- | --- | --- | --- | --- | --- | --- |
| | Dyestuff | Amount | Resin | Amount | Oxidizing agent | Amount | Resin | Amount |
| Ex. | | | | | | | | |
| 1 | 1 | 3.0 | 1 | 100.0 | 1 | 5.0 | 1 | 100.0 |
| 2 | 2 | 3.0 | 1 | 100.0 | 1 | 5.0 | 1 | 100.0 |
| 3 | 3 | 3.0 | 1 | 100.0 | 1 | 5.0 | 1 | 100.0 |
| 4 | 4 | 3.0 | 1 | 100.0 | 1 | 5.0 | 1 | 100.0 |
| 5 | 5 | 3.0 | 1 | 100.0 | 1 | 5.0 | 1 | 100.0 |
| 6 | 6 | 3.0 | 1 | 100.0 | 1 | 5.0 | 1 | 100.0 |
| 7 | 7 | 3.0 | 1 | 100.0 | 1 | 5.0 | 1 | 100.0 |
| 8 | 1 | 3.0 | 1 | 100.0 | 2 | 5.0 | 1 | 100.0 |
| 9 | 1 | 3.0 | 1 | 100.0 | 3 | 5.0 | 1 | 100.0 |
| 10 | 1 | 3.0 | 1 | 100.0 | 4 | 5.0 | 1 | 100.0 |
| 11 | 1 | 3.0 | 1 | 100.0 | 5 | 5.0 | 1 | 100.0 |
| 12 | 1 | 3.0 | 1 | 100.0 | 6 | 5.0 | 1 | 100.0 |
| 13 | 1 | 3.0 | 1 | 100.0 | 7 | 5.0 | 1 | 100.0 |
| 14 | 1 | 3.0 | 1 | 100.0 | 8 | 5.0 | 1 | 100.0 |
| 15 | 1 | 3.0 | 2 | 100.0 | 1 | 5.0 | 1 | 100.0 |
| 16 | 1 | 3.0 | Resin 1 | 100.0 | 1 | 5.0 | 1 | 100.0 |
| CEx. 1 | 1 | 0.1 | 1 | 100.0 | 1 | 5.0 | 1 | 100.0 |
| CEx. 2 | 1 | 3.0 | 1 | 100.0 | 1 | 0.1 | 1 | 100.0 |

Notes to Table 1 are as follows.
Ex. = Example, CEx. = Comparative Example Dyestuff 1 = 2-methoxy-phenothiazine, Dyestuff 2 = 2-acetyl-phenothiazine, Dyestuff 3 = 2-trifltioromethyl-phenothiazine, Dyestuff 4 = 3,7-dibromo-phenothiazine, Dyestuff 5 = 3-chloro-phenoxazine, Dyestuff 6 = phenothiazine, Dyestuff 7 = phenoxazine, oxidizing agent 1 = copper chloride (II), Oxidizing agent 2 = iron chloride (III), oxidizing agent 3 = tetrachloro-1,4-benzoquinone, Oxidizing agent 4 = 2,3-dochloro-5,6-dicyano-1,4-benzoquinone, oxidizing agent 5 = benzoyl peroxide, Oxidizing agent 6 = tert-butyl peroxybenzoate, Oxidizing agent 7 = mixture of tert-butyl peroxybenzoate : Aerosil 200 (silicon dioxide fine powder,supplied by Nippon Aerosil K.K.) = 5:40, Oxidizing agent 8 = supplied by Nippon Aerosil K.K.) = 5:40, Oxidizing agent 8 = nitrocellulose HIG200 (nitrated cotton, supplied by Asahi Chemical Industry Co., Ltd.)

TABLE 2

| Ex. | Color before measurement | 0° C. |
| --- | --- | --- |
| 1 | Colorless* | Reddish brown after 12 weeks, Color change: colorless → blue → violet → reddish brown |
| 2 | Yellow* | Green even after 12 weeks, Color change: yellow → green → blue → brown |
| 3 | Colorless* | Colorless even after 12 weeks, Color change: colorless → olive green → yellowish green |
| 4 | Light violet* | Sky blue after 2 weeks, Color change: Colorless → sky blue → blue |
| 5 | Colorless* | Sky blue after 2 weeks, Color change: colorless → green → blue → brown |
| 6 | Colorless* | Green even after 12 weeks, Color change: colorless → green → blue → red |
| 7 | Yellow* | Blue even after 12 weeks, Color change: yellow → sky blue → blue → brown |
| 8 | Light ocher* | Violet after 1 week, Color change: colorless → rose → violet |
| 9 | Colorless* | Colorless even after 12 weeks, Color change: colorless → orange |
| 10 | Colorless* | Green after 4 weeks, Color change: colorless → ivory → green → ocher |
| 11 | Colorless* | Orange after 4 weeks, Color change: colorless → orange |
| 12 | Colorless* | Blue even after 12 weeks, Color change: colorless → blue → violet → red |
| 13 | Colorless* | Red after 12 weeks, Color change: colorless → green → blue → violet → red |
| 14 | Colorless* | Colorless even after 12 weeks, Color change: colorless → green |
| 15 | Colorless* | Colorless even after 12 weeks, Color change: colorless → reddish brown |
| 16 | Colorless* | Violet after 8 weeks, Color change: colorless → blue → violet → reddish brown |
| CEx. 1 | Colorless* | Colorless even after 12 weeks, No change in color |
| CEx. 2 | Colorless* | Light yellowish green, Not easily distinguishable |

| Ex. | 20° C. | 100° C. |
| --- | --- | --- |
| 1 | Reddish brown after 4 weeks | Reddish brown after 1 day |
| 2 | Green after 12 weeks | Brown after 4 weeks |
| 3 | Colorless after 12 weeks | Yellowish green after 8 weeks |
| 4 | Sky blue after 1 week | Blue after 4 weeks |
| 5 | Brown after 12 weeks | Brown after 4 weeks |
| 6 | Blue even after 12 weeks | Red after 2 weeks |
| 7 | Brown after 4 weeks | Brown after 1 day |
| 8 | Violet after 4 days | Violet after 2 days |
| 9 | Colorless even after 12 weeks | Rose after 2 weeks |
| 10 | Ocher after 2 weeks | Ocher after 2 hours |
| 11 | orange after 8 hours | Orange after 1 hour |
| 12 | Red after 18 days | Red after 10 minutes |

TABLE 2-continued

| Ex. | Color before measurement 0° C. | |
|---|---|---|
| 13 | Orange after 1 week | Red after 2 minutes |
| 14 | Colorless even after 12 weeks | Green after 1 hour |
| 15 | Colorless even after 12 weeks | Reddish brown after 4 days |
| 16 | Reddish brown after 8 weeks | Reddish brown after 2 days |
| CEx. 1 | Colorless even after 12 weeks | Colorless even after 12 weeks |
| CEx. 2 | Light reddish brown after 4 weeks | Light reddish brown after 1 week |

Ex. = Example, CEx. = Comparative Example
*Color of layer containing agent A or B According to the method of indicating a time or a temperature-time accumulated value as a change in color and the indicator material, provided by the present invention, the passage of a predetermined period of time at a predetermined period of time can be easily and inexpensively indicated on the basis of a distinct change in hue obtained by a simple operation of bringing two agents into contact to initiate the polymerization of the oxidation-polymerizable dyestuff. The oxidation-polymerizable dyestuffs including phenothiazine or its derivatives can indicate the passage of time by developing colors with the passage of time and these oxidation-polymerizable dyestuffs are therefore suitable for showing periods of use (consumption periods, etc.). In particular, 2-methoxy-phenothiazine is a material which is colorless before being brought into contact with an oxidizing agent but turns green as soon as it is brought into contact with an oxidizing agent and shows a color change of blue→violet→reddish brown with the passage of time, and it is therefore perfectly suited as a visible indicator material.

Further, for the temperature and the time which are to be measured, the indicator material can be adjusted by selecting a resin for the carrier and the kind and amount of the oxidizing agent. It has been therefore found that the method and the indicator material of the present invention are effective for time measurement in a broad temperature range.

What is claimed is:

1. A method of indicating a passage of time or a temperature-time accumulated value as a color change, which comprises bringing an oxidation-polymerizable dyestuff of the following formula (1)

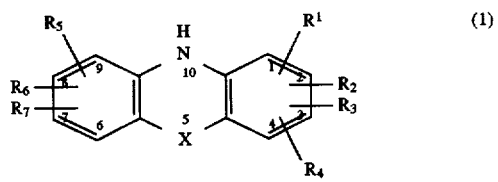

wherein each $R_1$ to $R_7$ is independently hydrogen, halogen, an alkyl group having 1 to 8 carbon atoms, aryl, substituted aryl, heterocyclic aryl, hydroxyl, amino, cyano, aldehyde, carbonyl or nitro, provided that a combination of adjacent substituents may form an aromatic ring, and X is sulfur, oxygen, selenium or tellurium, and an oxidizing agent into contact with each other to polymerize the oxidation-polymerizable dyestuff, and assessing the color change of the oxidation-polymerizable dyestuff to determine the passage of time or the temperature-time accumulated value.

2. A method according to claim 1, wherein the oxidizing agent is at least one member selected from the group consisting of metal salts, oxyacid salts, halogens, dimethylsulfoxide, quinones, naphthoquinones, carbonyl compounds, oxides, organic peroxides, organic peracids, peroxosulfates and nitro compounds.

3. An indicator material for indicating a passage of time or a temperature-time accumulated value of an article as a color change comprising an oxidation-polymerizable dyestuff of the following formula (1)

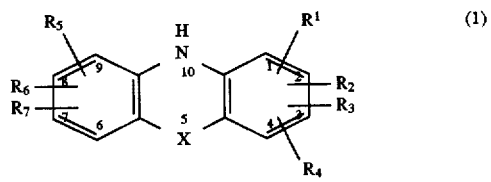

wherein each $R_1$ to $R_7$ is independently hydrogen, halogen, an alkyl group having 1 to 8 carbon atoms, aryl, substituted aryl, heterocyclic aryl, hydroxyl, amino, cyano, aldehyde, carbonyl or nitro, provided that a combination of adjacent substituents may form an aromatic ring, and X is sulfur, oxygen, selenium or tellurium, and an oxidizing agent, the oxidation-polymerizable dyestuff and the oxidizing agent being out of contact with each other before the indicator material is used, the oxidation-polymerizable dyestuff being polymerized with the passage of time to undergo a color change by bringing the oxidation-polymerizable dyestuff and the oxidizing agent into contact with each other when the indicator material is used.

4. An indicator material according claim 3, wherein the oxidation-polymerizable dyestuff is contained in a layer of a carrier and the oxidizing agent is contained in a layer of a carrier.

5. An indicator material according to claim 4, wherein the carrier containing the oxidation-polymerizable dyestuff is an adhesive material and/or the carrier containing the oxidizing agent is an adhesive material.

6. An indicator material according to claim 5, wherein the adhesive material is capable of diffusing the oxidation-polymerizable dyestuff and the oxidizing agent at a predetermined temperature.

7. An indicator material according to claim 4, wherein the carrier containing the oxidation-polymerizable dyestuff and/or the oxidizing agent is a resin layer laminated on a transparent substrate.

8. An indicator material according to claim 7, wherein the resin layer is a printed layer.

9. An indicator material according to claim 4, wherein the indicator material is formed of a layer containing the oxidation-polymerizable dyestuff in a carrier, a layer containing the oxidizing agent in a carrier and a spacing layer which is present between the layer containing the oxidation-polymerizable dyestuff and the layer containing the oxidizing agent and keeps these layers in a non-contact state.

10. An indicator material according to claim 9, wherein the spacing layer works to diffuse the oxidation-polymerizable dyestuff into the layer containing the oxidizing agent or to diffuse the oxidizing agent into the layer containing the oxidation-polymerizable dyestuff.

11. An indicator material according to claim 9, wherein the spacing layer is spacer material capable of bringing the layer containing the oxidation-polymerizable dyestuff and the layer containing the oxidizing agent into contact by an external pressure.

12. An indicator material according to claim 3, wherein the oxidizing agent in a non-contact state with the oxidation-polymerizable dyestuff is microencapsulated.

13. An indicator material according to claim 3, wherein the oxidizing agent is at least one member selected from the group consisting of metal salts, oxyacid salts, halogens, dimethylsulfoxide, quinones, naphthoquinones, carbonyl compounds, oxides, organic peroxides, organic peracids, peroxosulfates and nitro compounds.

* * * * *

UNITED STATES PATENT AND TRADEMARK OFFICE
CERTIFICATE OF CORRECTION

PATENT NO. : 5,756,356
DATED : May 26, 1998
INVENTOR(S) : Yanagi et al.

It is certified that error appears in the above-identified patent and that said Letters Patent is hereby corrected as shown below:

Column 16, line 38, before "claim" insert ---to---.

Signed and Sealed this

Thirteenth Day of April, 1999

*Attest:*

Q. TODD DICKINSON

*Attesting Officer*     *Acting Commissioner of Patents and Trademarks*